United States Patent [19]

Jaekel et al.

[11] Patent Number: 4,672,038
[45] Date of Patent: Jun. 9, 1987

[54] OPTICAL READOUT FOR BLOOD SAMPLE ANALYSIS

[75] Inventors: Robert W. Jaekel, Lindenhurst, Ill.; Dean M. Ball, Gainesville, Ga.

[73] Assignee: Abbott Laboratories, North Chicago, Ill.

[21] Appl. No.: 663,257

[22] Filed: Oct. 19, 1984

[51] Int. Cl.$^4$ .............................................. G01N 21/11
[52] U.S. Cl. .................................... 435/291; 435/808; 356/39; 356/436
[58] Field of Search ................. 435/808, 291; 356/39, 356/40, 41, 42, 436, 409, 414, 134

[56] References Cited

U.S. PATENT DOCUMENTS

| | | | |
|---|---|---|---|
| 3,622,795 | 11/1971 | Dorman | 356/39 X |
| 3,675,768 | 7/1972 | Sanchez | 356/39 X |
| 3,874,850 | 4/1975 | Sorensen | 356/40 X |
| 3,893,767 | 7/1975 | Fulwyler et al. | 356/39 |
| 3,989,381 | 11/1976 | Fulwyler | 356/39 |
| 4,101,276 | 7/1978 | Anderson | 356/39 X |
| 4,312,945 | 1/1982 | Yamada | 435/808 X |
| 4,515,274 | 5/1985 | Hollinger | 356/39 X |

*Primary Examiner*—Alan Cohan
*Attorney, Agent, or Firm*—Donald L. Corneglio

[57] ABSTRACT

Apparatus and method for detecting the presence of a substance in a biological material carried in a cartridge. Suitable substances are applied to such material, and adhere thereto if the substance sought to be detected is present. Optical means are then used to provide a signal indicative of the presence of such substance. The invention has particular application in detecting whether a quantity of human blood serum is infected with disease.

21 Claims, 5 Drawing Figures

U.S. Patent  Jun. 9, 1987  Sheet 1 of 2  4,672,038
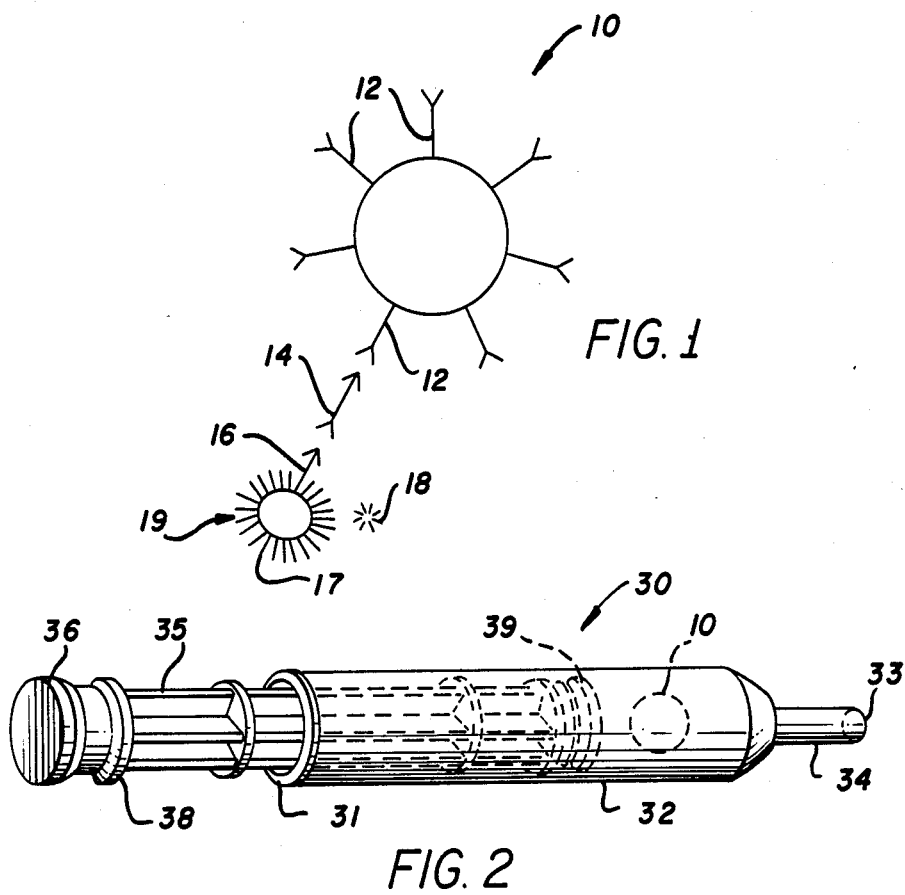
FIG. 1
FIG. 2
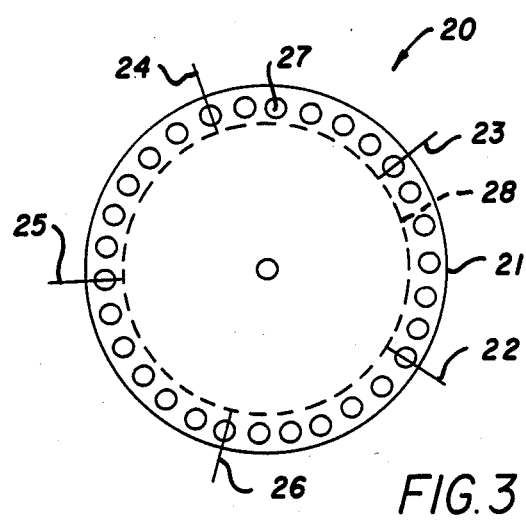
FIG. 3

OPTICAL READOUT FOR BLOOD SAMPLE ANALYSIS

BACKGROUND OF THE INVENTION

This invention relates to apparatus and methods for analyzing a biological material to ascertain whether a particular substance is present or absent. Most particularly, this invention relates to such apparatus and methods wherein the biological material is preferably human blood serum and the substance whose presence or absence is to be determined is preferably a composition indicative of disease, commonly referred to as an antigen. For example, in one aspect of this invention, human blood serum is analyzed to determine whether a hepatitis B surface antigen is present or absent.

Apparatus and methods for analyzing blood serum to ascertain whether a disease is present are especially important in situations where blood is donated by members of the public for the purpose of being subsequently administered to others by transfusion. In such cases it is necessary to analyze the donated blood to ensure that it is free from disease, lest the future user unknowingly contract that disease as a result of such transfusion. The disease for which analysis is most frequently conducted is hepatitis, though other diseases, including AIDS, may also be the subject of such analysis. Thus, though the descriptions referred to herein may specifically refer to hepatitis, it should be understood that such disease is exemplary rather than limitative, the scope of the invention being defined by the appended claims.

In one desirable apparatus for analyzing blood serum for substances indicative of disease, a rotatable incubation wheel is provided for moving a multiplicity of blood serum-containing cartridges to a plurality of operating stations. Such cartridges typically include a plunger, longitudinally movable through a cylindrical cavity containing the blood sample to be analyzed. A polystyrene bead coated with a disease specific antibody or antigen, is ordinarily placed inside the cylindrical cavity of the cartridge, where it can be contacted by a quantity of blood serum subsequently placed therein. As explained hereinafter, as the multiplicity of cartridges are moved by the incubation wheel through the various operating stations, various substances are introduced into the cartridge cavity where they are brought into contact with the antibody-coated or antigen-coated polystyrene bead. Depending on the nature of the substances so introduced, and whether the blood serum contains a substance characteristic of the disease that is the object of the analysis then being undertaken, the contents of the cavity may be assayed to provide a "positive" or "negative" indication of that disease.

Though blood analyzing apparatus and methods of the type described have been successfully employed, they are not without certain drawbacks and deficiencies. Accordingly, it is a primary object of this invention to provide improved apparatus and methods for determining whether a particular quantity of blood serum is characterized by a substance indicative of a particular disease. It is another object of this invention to provide such improved apparatus and methods which are highly reliable, and involve substantially hands-free operation. It is a further object of this invention to provide improved apparatus and methods of the type described wherein the analysis can be accomplished accurately, inexpensively and rapidly. It is yet another object of the invention to accomplish the foregoing, at least in part, by optical means.

SUMMARY OF THE INVENTION

The foregoing objects of the invention, along with numerous features and advantages, are achieved in an apparatus for detecting the presence of a substance in a biological material carried in a cartridge. The apparatus comprises chamber means for receiving a sample representative of the material to be analyzed, and a light source, aligned with the chamber means, adapted to apply a light beam to the sample. Light receiving means, extending into the chamber means, are adapted to receive the beam upon passage thereof through the sample. Optical means are adapted to receive the beam upon receipt by the light receiving means, and produce a signal if the substance is present in the material.

In another aspect of the invention there is provided a method for detecting the presence of a substance in a biological material carried in a cartridge comprising the steps of docking the cartridge in a cartridge port; discharging a sample, representative of the material, into chamber means communicating with the cartridge port; applying a beam of light through the sample to light receiving means; and producing a signal, corresponding to the light applied to the light receiving means, indicative of the presence of that substance in the material.

In one specific application the apparatus and methods of the invention may be employed to determine whether the biological material is infected with disease, i.e., whether the material contains a substance indicative of diseases such as hepatitis, AIDS, etc.

BRIEF DESCRIPTION OF THE DRAWINGS

An exemplary embodiment of the invention summarized above is shown in the accompanying drawings wherein:

FIG. 1 is a schematic representation of a bead, and substances adhering thereto, preferably used in connection with carrying out the present invention;

FIG. 2 is a schematic view of a cartridge containing the bead shown in FIG. 1, said cartridge being representative of the type used in connection with the present invention;

FIG. 3 is a very simplified schematic representation of apparatus of the type used in carrying out the present invention, said apparatus being adapted to carry a multiplicity of cartridges of the type shown in FIG. 2;

DETAILED DESCRIPTION OF AN EXEMPLARY EMBODIMENT OF THE INVENTION

Figures 4, 5:
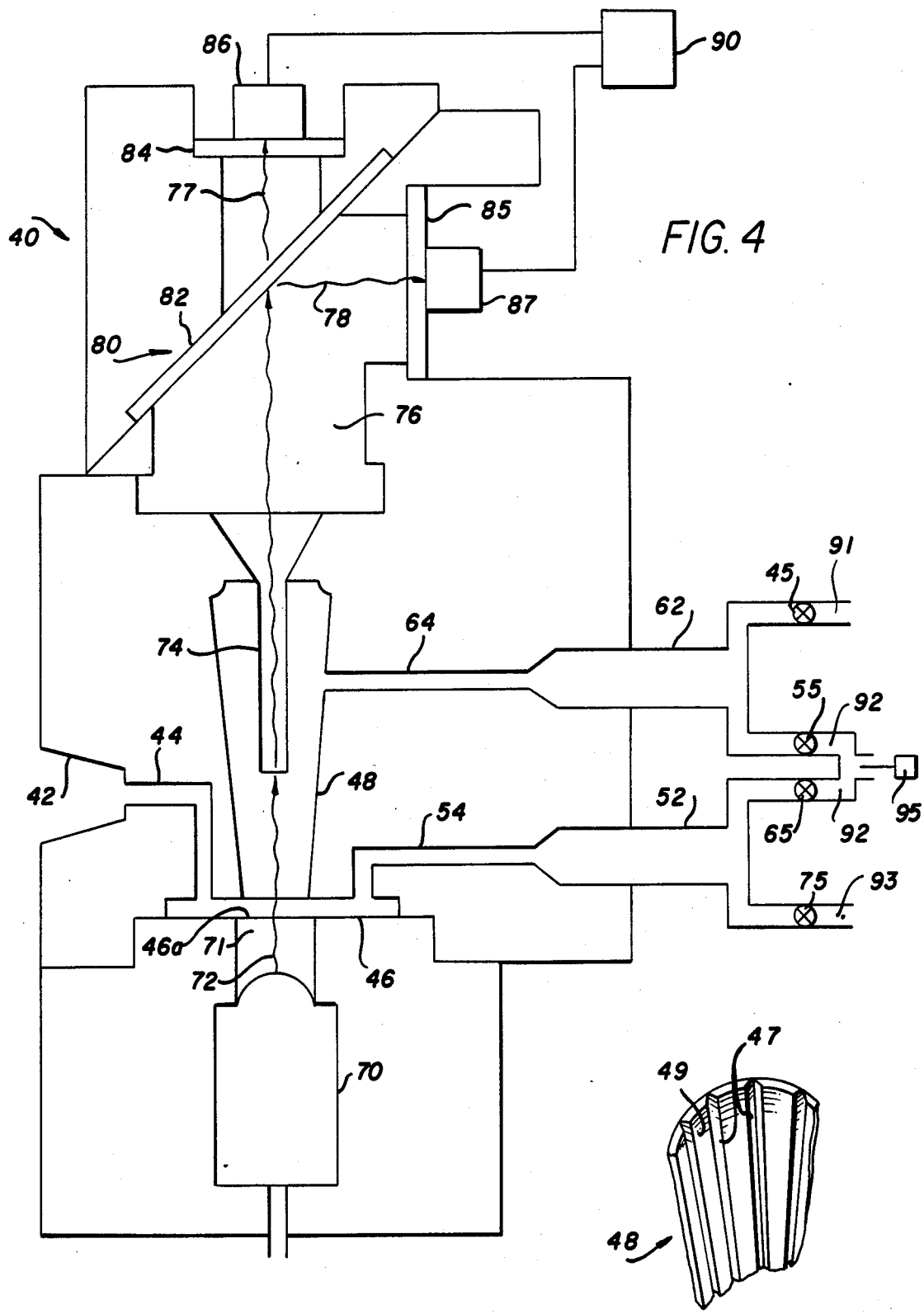
FIG. 4 is an optical readout device which, when read in light of the accompanying detailed description, represents a preferred embodiment of the invention.
FIG. 5 is an enlarged perspective view, partially cut-a-way, of a portion of the apparatus shown in FIG. 4.

As explained hereinbefore, the present invention pertains to apparatus and methods for analyzing biological material to determine whether a particular substance is present or absent. In a preferred form of the invention, the biological material to be analyzed is human blood serum, and the substance whose presence or absence is to be determined is a composition associated with the blood serum indicative of disease. Such composition usually contains a protein or carbohydrate which, when introduced into the body, stimulates the production of an antibody. The specific protein or carbohydrate composition which incites antibody production is commonly referred to as an antigen.

For exemplary purposes only, the detailed description that follows explains the apparatus and methods in terms of analyzing a quantity of human blood serum for purposes of determining whether that blood serum has a substance indicative of hepatitis, i.e., the blood serum is analyzed to determine whether an antigen corresponding to surface B hepatitis is present. It should be clearly understood, however, that the present invention is not so limited, but is also useful in analyzing blood serum to determine whether other substances, indicative of other diseases, may be present, in analyzing other biological fluids such as saliva, urine, throat swabs and the like, or in other applications not specifically described.

The present invention is preferably carried out by using means to which various substances are applied for purposes of conducting an analysis of a biological material such as human blood serum. As shown in FIG. 1, such means preferably take the form of a small bead 10, typically formed from polystyrene or some similar material, and typically being on the order of about ¼ inch in diameter. In accordance with well-known procedures, bead 10 is coated with an antibody associated with the particular disease that will be the subject of analysis. If this disease is hepatitis, for example, bead 10 will be coated with an antibody 12 to hepatitis B surface antigen, represented diagramatically by a plurality of inverted arrows, disposed about the periphery of bead 10. If another disease, such as AIDS, is the subject of analysis, bead 10 will, of course, be coated with a different antibody or AIDS specific agent.

In accordance with well-known and well-understood biological phenomenon which need not be described in detail herein, an antibody for a particular disease will adhere to the antigen corresponding to that disease when the antibody and the antigen are brought into contact under suitable conditions. Thus, if proper temperature and time parameters exist, a hepatitis B surface antigen 14, brought into contact with the antibody 12 to hepatitis B surface antigen covering bead 10, will become bonded thereto. Similarly, an antibody 16 congugated with an enzyme marker 17 to provide an antibody-enzyme conjugate 19, may become bonded to antigen 14 under proper time and temperature conditions. Antigen 14 and antibody-enzyme conjugate 19 are shown in diagrammatic form in FIG. 1.

Certain color-developing substances, commonly known as chromophores, and represented diagrammatically at 18 in FIG. 1, are known to change color in the presence of certain materials. One such chromophore is tetramethyl-benzidine. When the enzyme marker is horse radish peroxidase, tetramethyl-benzidine in a mixture including peroxide can be used to provide an indication that the hepatitis B surface antigen is present. The presence of this particular antigen in the blood serum under analysis is, of course, indicative of a "positive" test for hepatitis.

Bead 10, coated with appropriate antibody 12 is deposited in a laboratory cartridge 30 of the type shown in FIG. 2. Cartridge 30 has a cylindrical cavity 32 having a distal opening 31. At its proximal end cavity 32 tapers to a tip 34 terminating in a proximal opening 33. In this exemplary embodiment, bead 10, coated with antibody 12, is deposited in cavity 32 before analysis begins.

Cartridge 30 further includes a plunger 35 having a distal handle 36 formed with a flange 38 to assist in actuation of the plunger. Associated with plunger 35 is at least one sealing ring 39 which serves as a barrier to fluid in cavity 32, and which forces such fluid through tip 34 and out proximal opening 33 when plunger 35 is urged through cavity 32.

Initially, plunger 35 is retracted from cavity 32 so that bead 10, coated with antibody 12, can be put into cavity 32 via distal opening 31. Means (not shown) may then be used to draw a quantity of material, such as blood serum, into cavity 32 of cartridge 30, permitting that material to contact the antibody-coated bead 10. Alternatively, pipetting may be used so that the material to be analyzed will not enter cavity 32 until a timed operation is about to commence. This enables one to accurately control the time in which the material is in contact with the antibody 12 on bead 10.

Cartridge 30, containing both the material to be analyzed and the bead 10, may then be loaded on an apparatus of the type represented schematically by apparatus 20 in FIG. 3. Apparatus 20 includes a rotating incubation wheel 21 having a plurality of cartridge receiving cavities 27 and an incubation heater strip schematically illustrated at 28. Apparatus 20 further includes a plurality of operating stations identified by reference numerals 22-26. Operating station 22 represents a load station where cartridges containing the material to be analyzed and the bead 10 are sequentially loaded onto wheel 21. For exemplary purposes, the material to be analyzed is referred to hereinafter as blood serum.

After cartridge 30 has been loaded onto incubation wheel 21, and the blood serum is brought into contact with antibody-coated bead 10, wheel 21 is preferably rotated for approximately 37 minutes while subjecting cartridge 30 to temperatures of about 40° C. It has been found that these parameters of time and temperature represent a sufficient incubation period for any hepatitis B surface antigen associated with the blood serum in cavity 31 of cartridge 30 to bond to the antibody 12 coated on bead 10. Thus, if the blood serum in cartridge 30 is infected with hepatitis, hepatitis B surface antigen will be present, and it will become bonded to the hepatitis antibody coating bead 10 after the incubation period has been concluded. On the other hand, if the blood serum in cartridge 30 is not infected with hepatitis, there will be no hepatitis B surface antigen present in the blood serum, and therefore no such antigen will be available for bonding to the antibody-coated surface of bead 10.

After cartridge 30 has been rotated by wheel 21 for a period of time sufficient to cause any hepatitis antigen associated with the blood serum contained in cavity 32 to become bonded to the antibody-coated surface of bead 10, the apparatus 20 causes wheel 21 to stop at operating station 23. At operating station 23 the cavity 32 is washed, and then the contents, i.e., bead 10 with antibody 12 and antigen 14 successively bonded thereto, is exposed to an antibody-enzyme conjugate 19. In this exemplary embodiment enzyme marker 17 is a specific compound known as horse radish peroxidase. Being hepatitis specific, antibody 16 (and enzyme marker 17) bonds to antigen 14 for reasons previously explained. In summary, at operating station 23 the portion of the blood serum which did not bond to the antibody-coated bead 10 is first expelled from cavity 32, and the cavity is then washed to remove residue therein. When this washing operation is completed, the antibody-enzyme conjugate 19 is introduced into cavity 32.

After antibody-enzyme conjugate 19 has been introduced into cavity 32, wheel 21 is again operated, causing cartridge 30 to be rotated for about 15 minutes at a temperature of approximately 40° C. until the reaction is complete. When this secon incubation period is completed, wheel 21 stops at operating station 24 where another washing cycle is undertaken to remove all conjugate and enzyme material from cavity 32 which did not bond to the bead 10 during the second incubation process. When the unbonded material is removed, the color-developing chromophore mixture is introduced into cavity 32. This chromophore mixture preferably includes the chromophore tetramethylbenzidine mixed with peroxide. Tetramethylbenzidine will turn blue in the presence of peroxide if the enzyme horse radish peroxidase is present. Of course, antibody-enzyme conjugate 19 is present only if bonded to antigen 14; and antigen 14 is present only if the blood serum originally introduced into the cartridge 30 was infected with hepatitis. If the blood serum was not so infected, there would have been no antigen 14 bonded to the antibody-coated bead 10, no conjugate bonded to the antigen 14, and therefore no enzyme 17 to cause chromophore 18 to change color. In short, the changing of chromophore 18 to a blue color is a "positive" indication that the blood serum originally deposited in cavity 32 of cartridge 30 was infected with hepatitis.

After the chromophore 18 is introduced, the cartridge 30 is again rotated on wheel 21 for about eight minutes at approximatel 40° C. When this final incubation period is complete wheel 21 is stopped at operating station 25. It is at this operating station where a sample of the chromophore 18, representative of the blood serum originally deposited in cartridge 30, is ejected into a chamber and analyzed by an optical readout device. If the chromophore 18 turned blue as a result of the presence of enzyme 17, the optical readout device will develop a signal indicative of a "positive" hepatitis reaction. The absence of this signal, on the other hand, is indicative of a "negative" hepatitis reaction.

The chromophore 18 is characterized by its ability to absorb certain light components and not others. For example, the chromophore mixture used in the present invention, when incubated with an enzyme, absorbs light components at the red end of the spectrum (650 nm) to a far greater extent than it absorbs light components at the blue end of the spectrum (490 nm). As a result, light passing through the chromophore 18 will be characterized by a relative abundance of blue light, and a relative lack of red light.

After the chromophore is ejected at operating station 25, and the optical analysis is undertaken, wheel 21 moves cartridge 30 to operating station 26. It is at operating station 26 that cartridge 30 is removed from wheel 21 of apparatus 20. It should be understood that throughout the course of this analysis, other cartridges may be simultaneously loaded, washed, and removed, whereby the results of numerous analyses can be completed during the time any single cartridge is loaded at operating station 22 and subsequently removed from apparatus 20 at operating station 26.

Referring now to FIG. 4, there is shown an optical readout device 40 of the type that would be positioned at operating station 25 of apparatus 20. Optical readout device 40 includes a docking port 42 configured and adapted to receive cartridge 30. In particular, docking port 42 has a docking passage 44 adapted to communicate with the proximal tip 34 of cartridge 30. Thus, when cartridge 30 is docked in port 42, and its contents expelled, a sample of the chromophore 18 will pass via proximal opening 33 of cartridge 30 into docking passage 44. Docking passage 44 communicates with a chamber 48 by way of a chamber passage 46. For reasons that will be apparent hereinafter, at least a portion of chamber passage 46, for example, portion 46a, is formed from a translucent material such as optical glass to allow a beam of light to pass therethrough.

Optical readout 40 further includes a wash port 52 coupled to chamber passage 46 via a wash passage 54, and a waste port 62 coupled to chamber 48 via waste passage 64. Waste port 62 is coupled to a vent tube 91 and a waste tube 92, while wash port 52 is coupled to waste tube 92 and wash tube 93. Valves 45, 55, 65 and 75 may be disposed, respectively, between waste port 62 and vent tube 91, between waste port 62 and waste tube 92, between wash port 52 and waste tube 92 and between wash port 52 and wash tube 93. If desired, valves 45, 55, 65 and 75 can be used to control the flow of fluid between the various tubes 91, 92 and 93 and chamber 48; with the flow of fluid being driven by cartridge plunger 35 or by maintaining waste tube 92 under a vacuum as indicated schematically by vacuum source 95.

Optical readout 40 further includes optical means 80 comprising, inter alia, a light source 70, light receiving means 74, a beam splitter 82, bandpass filters 84 and 85, light responsive elements 86, 87, and electronic means 90. Light source 70, disposed below chamber passage 46, is adapted to project a beam of light 72 via a light path 71 through the transluscent portion 46a of chamber passage 46 and into chamber 48. Beam 72 will pass through the chromophore 18 in chamber 48 until intercepted by light receiving means 74, which preferably takes the form of a light pipe. Beam 72 is directed so that it does not cross any of the walls of chamber 48 so that beam 72 will not be partially blocked or deflected by contaminents or air bubbles which might be adhered to the surface of the walls. Light receiving means 74 has a depending end 75 which desirably extends into chamber 48 above chamber passage 46 but below the confluence of waste passage 64 with chamber 48. The chromophore 18 ejected from cartridge 30 preferably fills chamber 48 above depending end 75 of light receiving means 74. If, however, the level of chromophore 18 rises too high in chamber 48, excess can be removed via waste passage 64.

Light receiving means 74 passes the beam of light 72 received from source 70 to beam splitter 82, preferably in the form of a red reflective dichroic plane. Beam splitter 82 thus splits the beam of light 72 into a first light component 77 (blue) characterized by first wavelengths below about 550 nm, and a second light component 78 (red) characterized by second wavelengths above about 550 nm. Light component 77 is passed from beam splitter 82 through a 490 nm light filter 84 and associated optical elements (not shown) to light responsive element 86 which, in this exemplary embodiment, is a photo diode. Light responsive element 86 produces an electrical signal corresponding to the strength of the impinging light component 77, sometimes referred to herein as a blue test signal. Similarly, light component 78 is reflected from beam splitter 82 through a 650 nm light filter 85 and associated optical elements (not shown) to a light responsive element 87 which, in this exemplary embodiment, is also a photo diode. Light responsive element 87 also produces an electrical signal corresponding to the strength of the impinging light component 78, sometimes referred to herein as a red test signal. The blue and red test signals produced by light responsive elements are passed to electronic means 90 for subsequent manipulation.

After the signals at light responsive elements 86, 87 have been passed to electronic means 90, chamber 48 is preferably emptied and washed, removing any residue of the sample of chromophore 18. Evacuation is accomplished by opening valves 45 and 65 and closing valves 55 and 75, which places waste port 62 in communication with vent tube 91 and wash port 52 in communication with waste tube 92. Because waste tube 92 is under a vacuum, the fluid in chamber 48 will be sucked out of chamber 48 via wash passage 54, wash port 52 and waste port 92. When the contents of chamber 48 have been removed in the manner described, chamber 48 is washed of all chromophore residue. This is accomplished by opening valves 55 and 75, and closing valves 45 and 65. Wash fluid is supplied to wash tube 93 and passes to wash port 52 through chamber passage 46 through chamber 48, to waste port 62 and waste tube 92.

When the chamber 48 has been cleaned, it is filled with a reference fluid, such as clean water. This is accomplished by opening valve 45 and closing valves 55, 65 and 75 at the end of the above-described washing operation. Light source 70 is again operated, and an analysis is performed in substantially the same manner described when the sample of chromophore 18 was passed into chamber 48. Since the reference fluid does not absorb selected light in the same manner as the chromophore 18, the light components 77 and 78 passing through beam splitter 72 are not characterized by the same disparity in strength. As a result, the signals produced by light responsive elements 86, 87, sometimes referred to herein as blue and red reference signals, when the reference fluid is present, are necessarily different from the blue and red test signals. The blue and red reference signals are also applied to electronic means 90.

After the reference signals are processed, the reference fluid is evacuated from chamber 48 in the same manner as the chromophore. Before the reference fluid evacuation is stopped, the cartridge 30 is slowly removed from the docking port 42. This allows air to be pulled into the docking port pulling any residue into waste. After the cartridge has been fully removed, valve 45 is opened and valves 55, 65 and 75 are closed to prepare to receive the next chromophore sample.

Electronic means 90 generates a first absorbance signal corresponding to the logarithm of the ratio of the red reference signal and the red test signal. Similarly, electronic means 90 also generates a second absorbance signal corresponding to the logarithm of the ratio of the blue reference signal and the blue test signal. Electronic means 90 further generates an output signal indicative of the difference between the first and second absorbance signals. The greater the output signal, the more hepatitis antigen was present in the blood serum under analysis. The smaller the output signal, the less hepatitis antigen was present. A relatively large output signal is therefore indicative that the blood serum was infected with hepatitis.

Referring now to FIG. 5 there is shown a portion of chamber 48 including a portion of the interior surface 49. Interior surface 49 is preferably formed from hydrophobic material such as Delrin. Surface 49 is further characterized by a plurality of grooves 47 each preferably having a V-shaped cross-section with a sharply tapered bottom. Grooves 47 help carry air bubbles that may be associated with the fluid passed into chamber 48 in an upwardly direction so that such bubbles do not interfere with the application of beam 72 from source 70, through the fluid in chamber 48 in light receiving means 74. The fact that surface 49 is made from hydrophobic material further promotes this result.

What has been described is a novel optical readout device useful in detecting the presence of disease in a quantity of blood serum. As explained above, it is believed that those skilled in the art will appreciate that the device disclosed herein will have many applications beyond those referred to herein, and therefore the exemplary embodiment so disclosed should not be construed as limitative. Moreover, though the exemplary embodiment referred to above is preferred, those skilled in the art are likely to devise numerous variations and modifications which do not part from the true scope of the invention. Accordingly, all such variations and modifications are intended to be covered by the appended claims.

We claim:

1. In an apparatus for detecting the presence of a substance in a biological material carried in a cartridge, an optical analyzing station comprising:
   chamber means for receiving a sample representative of said material from said cartridge;
   a light source adapted to apply a light beam to said sample;
   light receiving means having one end extending into said chamber adapted to receive said beam upon passage thereof through said sample;
   optical means, adapted to receive said beam upon receipt thereof by said light receiving means, producing a signal indicative of the presence of said substance in said material;
   a waste passage communicating with said chamber means at a position above said end of said light receiving means; and
   a wash passage communicating with said chamber means at a position below said end of said light receiving means.

2. The apparatus defined in claim 1 wherein said one end of said light receiving means is in contact with said sample.

3. The apparatus defined in claim 1 wherein said light receiving means is a light pipe.

4. The apparatus defined in claim 1 further includes docking means for receiving said cartridge, and means causing said sample to be discharged into said chamber means when said cartridge is received at said docking means.

5. The apparatus defined in claim 1 further includes valve means communicating with said wash passage and said waste passage, operable for controlling flow into and out of said wash passage and said waste passage.

6. The apparatus defined in claim 5 wherein said valve means are operated to allow said sample in said chamber means to escape after said biological material has been analyzed.

7. The apparatus defined in claim 1 further includes means for flushing said chamber means with fluid after said biological material has been analyzed.

8. The apparatus defined in claim 1 wherein said chamber means has a surface formed from substantially hydrophobic material, said surface defining sharply tapered grooves for promoting passage of bubbles through said chamber means.

9. The apparatus defined in claim 8 wherein said grooves have a substantially V-shaped cross-section.

10. The apparatus defined in claim 1 wherein said optical means include means for separating said beam into a light component indicative of the presence of said substance, means for filtering said component, and means for producing an electrical signal corresponding to the strength of said component so filtered.

11. The apparatus defined in claim 1 wherein said optical means include:
   means for separating said beam into a first test component and a second test component when said sample is in said chamber means; and
   means for removing said sample from said chamber means and passing a reference fluid thereto, thereby permitting production of a first reference component and a second reference component by applying said beam to said reference fluid.

12. The apparatus defined in claim 11 wherein said optical means further include:
   a first photo responsive element adapted to receive said first test component and said first reference component and produce, respectively, a first test signal and a first reference signal; and
   a second photo responsive element adapted to receive said second test component and said second reference component and produce, respectively, a second test signal and a second reference signal.

13. The apparatus defined in claim 12 wherein said optical means further includes electronic means adapted to receive said test signals and said reference signals and produce a first absorbance signal corresponding to the logarithm of the ratio of said first test signal and said first reference signal, and produce a second absorbance signal corresponding to the logarithm of the ratio of said second test signal and said second reference signal.

14. The apparatus defined in claim 13 wherein said electronic means further produce an output signal corresponding to the difference between said first and second absorbance signals.

15. A method for detecting the presence of a substance in a biological material carried in a cartridge comprising the following steps:

(a) docking said cartridge in a cartridge port;
(b) discharging a sample representative of said material into chamber means communicating with said port;
(c) applying a first beam of light through said sample to a light pipe extending into said sample;
(d) producing a signal, corresponding to said light applied to said light pipe indicative of the presence of said substance;
(e) removing said sample from said chamber means by a wash passage located below said end of said light pipe;
(f) flushing said chamber means by supplying a wash via said wash passage and removing said wash via a waste passage located above said end of said light pipe;
(g) supplying a reference fluid to said chamber means;
(h) applying a second beam of light through said reference to said light pipe;
(i) producing a signal corresponding to said light applied to said light pipe;
(j) comparing the signals obtained from steps (d) and (i).

16. The method defined in claim 15 further includes the step of separating said beams of light into first and second components.

17. The method defined in claim 16 further includes the step of applying said components to photo responsive means for producing first and second signals.

18. The method defined in claim 17 further includes the step of filtering said components prior to applying said components to said photo responsive means.

19. The method defined in claim 17 further includes the step of removing said sample from said chamber means after applying said beam of light to said sample.

20. The method defined in claim 18 further includes the step of applying said signals produced from said sample and said reference to electronic means for producing a first absorbance signal corresponding to the logarithm of the ratio between one of said sample and said reference signals, and a second absorbance signal corresponding to the logarithm of the ratio between the other of said sample and reference signals.

21. The method defined in claim 15 wherein said applying step comprises applying a beam of light through said sample along a path that does not cross any surfaces of said chamber means.

* * * * *